(12) United States Patent
Fehling et al.

(10) Patent No.: US 11,806,003 B2
(45) Date of Patent: Nov. 7, 2023

(54) SURGICAL RETRACTOR FOR CARDIAC SURGERY

(71) Applicant: FEHLING INSTRUMENTS GmbH &Co. KG, Karlstein (DE)

(72) Inventors: Gerald Fehling, Alzenau (DE); Hendrik Treede, Bonn (DE)

(73) Assignee: FEHLING INSTRUMENTS GmbH & Co. KG, Karlstein (DE)

( * ) Notice: Subject to any disclaimer, the term of this patent is extended or adjusted under 35 U.S.C. 154(b) by 0 days.

(21) Appl. No.: 17/816,964

(22) Filed: Aug. 2, 2022

(65) Prior Publication Data
US 2023/0039297 A1 Feb. 9, 2023

(30) Foreign Application Priority Data
Aug. 6, 2021 (EP) ..................................... 21190196

(51) Int. Cl.
*A61B 17/02* (2006.01)
(52) U.S. Cl.
CPC ...... *A61B 17/02* (2013.01); *A61B 2017/0237* (2013.01)
(58) Field of Classification Search
CPC ............ A61B 17/02; A61B 2017/0237; A61B 17/0206; A61B 17/2018
USPC ................................................ 600/201–245
See application file for complete search history.

(56) References Cited

U.S. PATENT DOCUMENTS

| | | | | |
|---|---|---|---|---|
| 5,779,629 | A * | 7/1998 | Hohlen | A61B 17/0293 600/233 |
| 7,276,024 | B1 * | 10/2007 | Royse | A61B 17/02 600/210 |
| 8,523,769 | B2 | 9/2013 | Fehling | |
| 2004/0193018 | A1 * | 9/2004 | Thalgott | A61B 17/02 600/227 |
| 2011/0275902 | A1 * | 11/2011 | Bucholz | A61B 17/0293 600/206 |
| 2018/0317900 | A1 * | 11/2018 | Gdowski | A61B 1/32 |

FOREIGN PATENT DOCUMENTS

| | | |
|---|---|---|
| WO | 0106934 | 2/2001 |
| WO | 2013117264 | 8/2013 |

* cited by examiner

*Primary Examiner* — Eduardo C Robert
*Assistant Examiner* — Tara Rose E Carter
(74) *Attorney, Agent, or Firm* — Akerman LLP; Peter A. Chiabotti

(57) ABSTRACT

A surgical retractor for cardiac surgery with a hollow tube-shaped first base body with a first base body longitudinal axis on which at least one first rib comprising a first end, a second end, and a first rib longitudinal axis is laterally disposed with its first end, and with a second base body with a second base body longitudinal axis on which at least one second rib comprising a first end, a second end, and a second rib longitudinal axis is laterally disposed with its first end, wherein in the first base body a first transport rod with a first transport rod longitudinal axis is disposed such that it is supported rotatably about the first transport rod longitudinal axis, wherein the at least one second rib penetrates the first base body in a through hole transversely to the first base body longitudinal axis, and wherein the at least one second rib comprises several recesses spaced apart with respect to one another along the second rib longitudinal axis, and the first transport rod comprises at least one projection cooperating with the recesses.

17 Claims, 6 Drawing Sheets

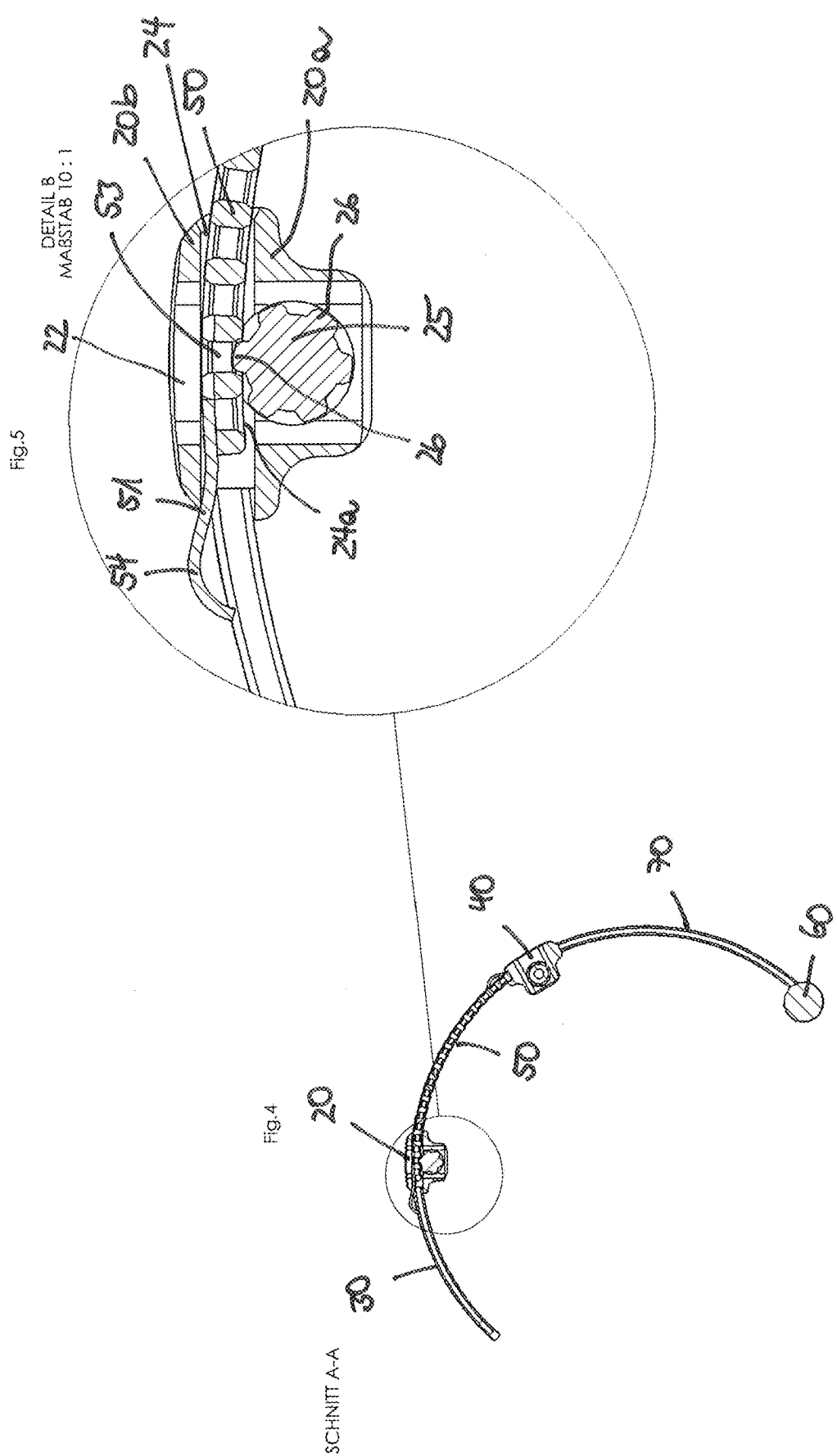

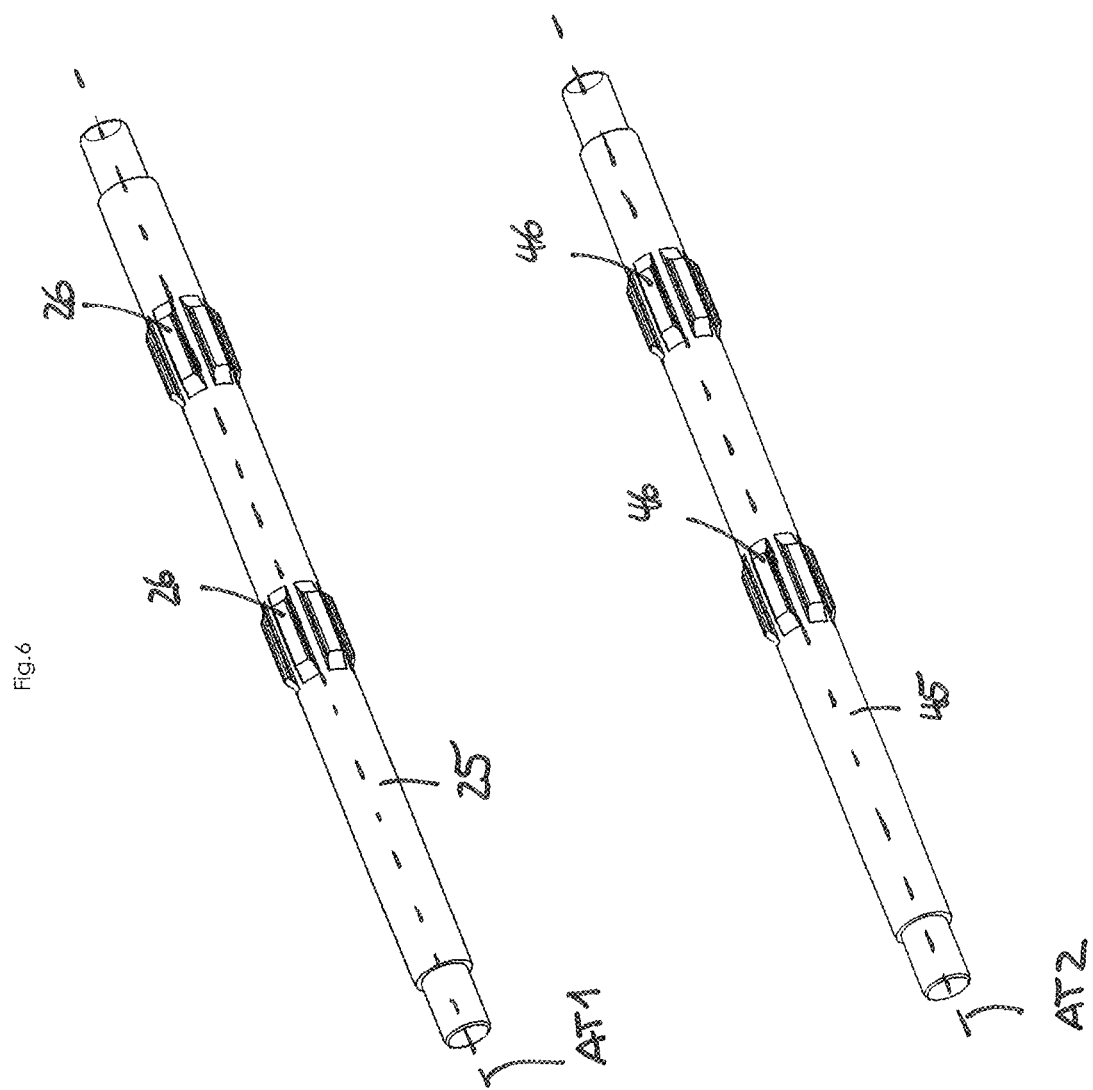

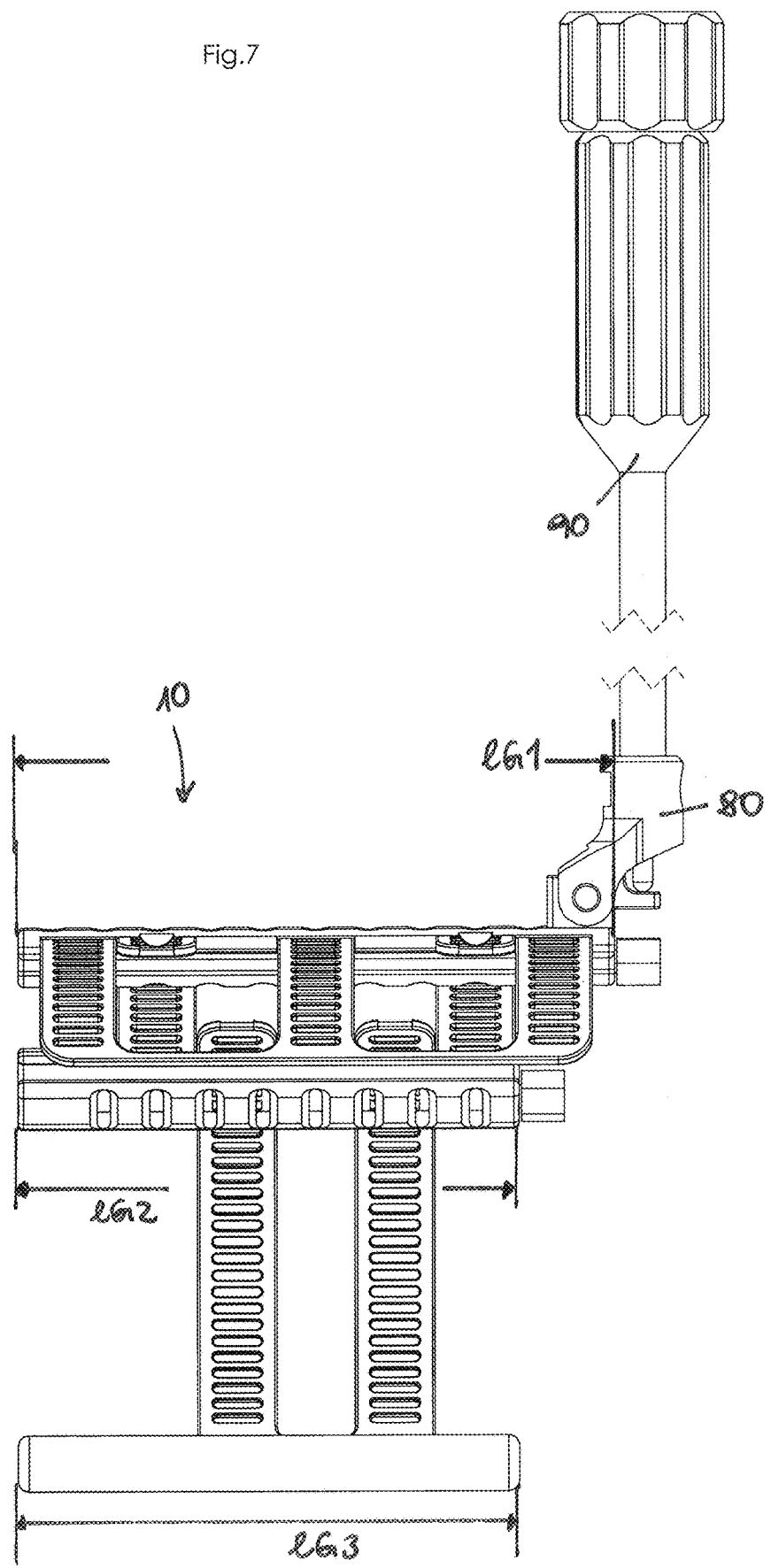

SURGICAL RETRACTOR FOR CARDIAC SURGERY

CROSS REFERENCE TO RELATED APPLICATIONS

This application claims priority to European Patent Application No. 21190196.2, filed Aug. 6, 2021, the entirety of which is incorporated by reference.

BACKGROUND

The present application relates to a surgical retractor for cardiac surgery.

EP 2 124 757 B1 discloses an atrial retractor for use in a surgical intervention on the heart, in which a retractor blade is disposed on a distal end of a handle, and wherein on the retractor blade a hinged flap is disposed which can be swivelled out for the enlargement of the contact area. For swivelling out the flap appropriate space is required.

SUMMARY

The present disclosure therefore addresses the problem of providing a surgical retractor for cardiac surgery which, after its introduction through an access, can be enlarged in simple manner with respect to its retaining area.

According to the present disclosure the problem is resolved through a surgical retractor for cardiac surgery having the features and structures recited herein.

The surgical retractor according to the present disclosure for cardiac surgery comprises a hollow tube-shaped first base body with a first base body longitudinal axis, on which first base body at least one first rib comprising a first end, a second end, and a first rib longitudinal axis is disposed laterally [and perpendicularly] with its first end, and a second base body with a second base body longitudinal axis, on which second base body at least one second rib comprising a first end, a second end, and a second rib longitudinal axis is disposed laterally [and perpendicularly] with its first end, wherein in the first base body a first transport rod with a first transport rod longitudinal axis is disposed such that it is supported rotatably about the first transport rod longitudinal axis, wherein the at least one second rib penetrates the first base body in a through hole transversely to the first base body longitudinal axis, and wherein the at least one second rib comprises several recesses spaced apart with respect to one another along the second rib longitudinal axis, and the first transport rod comprises at least one projection cooperating with the recesses.

Such embodiment enables a lateral broadening of the contact area, spanned by the first and the second ribs of the retractor, in particular without having to provide space for an expansive swivel movement. Due to the cooperation of the projection[s] disposed on the transport rod with the recesses of the at least one second rib, by rotating the transport rod about its transport rod longitudinal axis the second is moved through the through hole, in particular transversely to the first base body longitudinal axis. If, for example, in a first position the second base body is in contact on the first base body, by rotation of the transport rod the at least one second rib can be laterally extended whereby the distance between the second base body and the first base body is increased. The contact area of the retractor is thereby also increased.

Unless explicitly stated otherwise, if in the following the term "rib" is used, this term is intended to comprise the first as well as also the second and, if applicable, also the third or further ribs. The same applies also, unless explicitly stated otherwise, to the use of the designation "base body" and "transport rods".

To enable improved cleaning, the recesses in the at least one second rib can also be implemented as continuous recesses. Further, on the at least one first rib corresponding recesses can also be disposed.

The first transport rod preferably comprises several projections which, in particular, are implemented in the manner of a toothed wheel. Such an implementation can enable the reliable and simple-to-clean transport mechanism in a structurally simple manner.

An advantageous further development of the present disclosure provides for the first transport rod to comprise a non-round actuation section, preferably an actuation section with a hexagonal cross section, wherein, preferably, the actuation section projects from the base body on a front face of the first base body. Such actuation section can in simple manner permits a rotation of the transport rod using an appropriate tool, for example in the manner of a wrench.

According to a preferred embodiment of the present disclosure the first base body comprises three first ribs spaced apart along the first base body longitudinal axis. The first ribs can herein be connected with one another at their second ends by means of a cross web.

Such frame-like implementation enables the most stability feasible of the retractor.

The second base body preferably comprises two second ribs spaced apart along the second base body longitudinal axis. Each of these preferably engages into the interspace between, in each instance, two first ribs. Such an implementation can enable high stability at the simplest feasible compact structure.

During a transport movement one side edge of the at least one second rib is advantageously guided so as to glide along a side edge of the at least one first rib, preferably in the manner of a tongue-and-groove joint. The stability can thereby also be increased during a transport movement.

A preferred further development of the present disclosure provides for the second base body to be of a length that is less than a length of the first base body, preferably less by at least 10% of the length of the first base body. The retractor can thereby be better adapted to the anatomical conditions within the heart.

According to an especially preferred further development of the present disclosure a third base body with a third base body longitudinal axis is provided on which third base body at least one third rib comprising a first end, a second end, and a third rib longitudinal axis is laterally disposed with its first end, wherein the second base body is implemented in the form of a hollow tube, and in the second base body a second transport rod with a second transport rod longitudinal axis is disposed such that it is implemented to be supported rotatably about the second transport rod longitudinal axis, wherein the at least one third rib penetrates the second base body in a through hole transversely to the second base body longitudinal axis, and wherein the at least one third rib comprises several recesses disposed spaced apart with respect to one another along the third rib longitudinal axis, and the second transport rod comprises at least one projection cooperating with the recesses. A third such base body enables a further broadening of the contact area of the retractor. However, for its introduction through an access the retractor can be pushed together or contracted such that its width corresponds substantially to the length of the first rib plus the width of the base body. In its completely pushed-apart state, the width can therewith be approximately tripled in comparison to the width in its completely contracted state.

Analogously, a fourth base body and optionally further base bodies can also be provided.

The third base body preferably comprises two third ribs disposed spaced apart along the third base body longitudinal axis in order to be able to span as sufficient as feasible a contact area.

According to an advantageous embodiment of the present disclosure the width of a rib corresponds approximately to the length of the first base body divided by the number of all ribs of the retractor. Stated differently, the width of a rib is preferably chosen to be as large as feasible in order to enable as high a stability and as large a contact area as feasible.

An especially preferred embodiment of the present disclosure provides for the ribs to be curved along their rib longitudinal axis. Such an implementation enables good adaptation of the retractor to the anatomical conditions.

According to an advantageous implementation of the present disclosure the through hole comprises a curved contact area for the rib whereby the stability of the retractor can be increased and the guidance of the ribs during the transport can be improved.

The ribs preferably comprise on their second end a preferably elastically resilient implemented abutment element. The abutment element prevents the unintentional rotation of the ribs out of the through hole of the particular base body. If the abutment element is developed elastically resilient, this can enable an intentional rotation out thereby that deliberately a higher force is applied, for example for the purpose of disassembling the retractor for cleaning purposes or when exchanging ribs.

The hollow tube-form base bodies advantageously comprise at least one flush opening, preferably several flush openings, to enable improved cleanability.

It is especially preferred for a receiving element to be disposed on the first base body for receiving a holding and/or manipulation grip. By means of the holding and/or manipulation grip the retractor can be set in through an access during a surgical intervention and be positioned in a desired position and/or orientation.

The surgical retractor according to the present disclosure is applied in particular in cardiac surgery.

BRIEF DESCRIPTION OF DRAWINGS

An embodiment example of the present disclosure will be explained in detail in conjunction with the following Figures. Therein depict FIG. 1 a perspective view of an embodiment example of a surgical retractor according to the present disclosure for cardiac surgery, FIG. 2 a further perspective view of the retractor according to FIG. 1, FIG. 3 a top view onto the retractor according to FIG. 1, FIG. 4 a section along line A-A [not indicated] in FIG. 3, FIG. 5 a cutaway enlargement from FIG. 4, FIG. 6 a perspective view of both transport rods of the retractor according to FIG. 1 and FIG. 7 the retractor according to FIG. 1 with a holding and/or manipulation grip disposed thereon.

DETAILED DESCRIPTION

Figure 1:
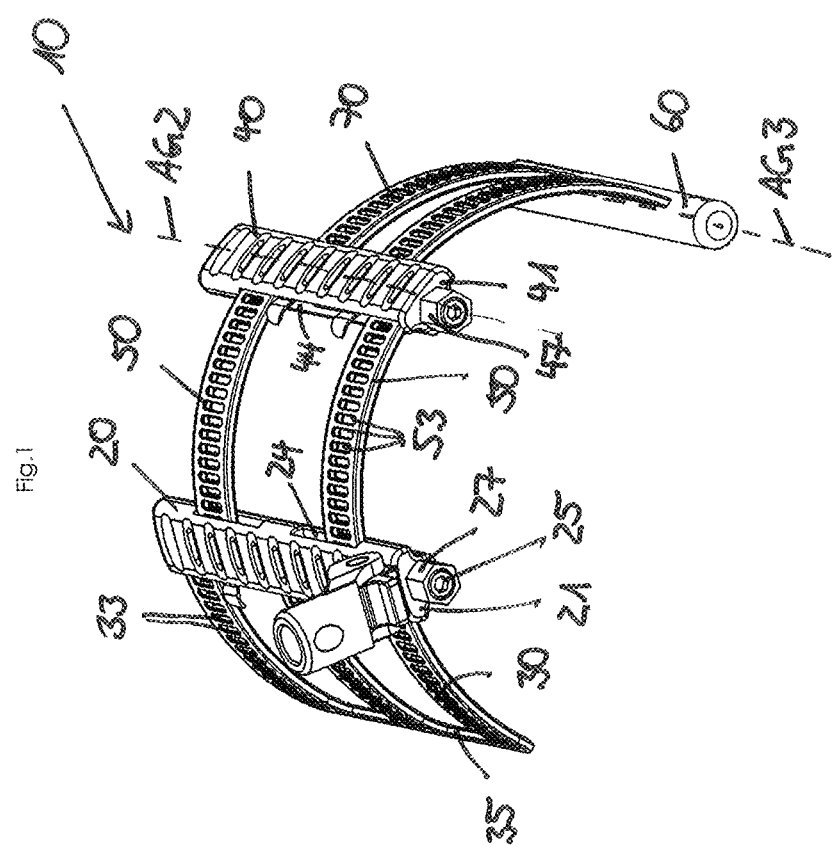
Figure 2:
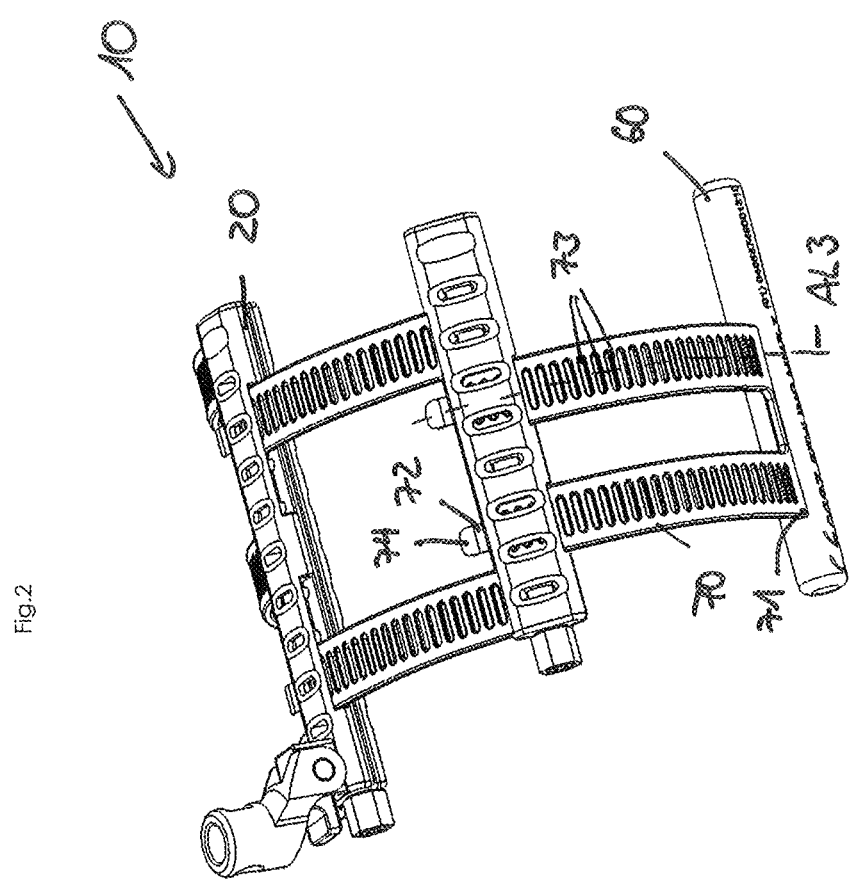
Figure 3:
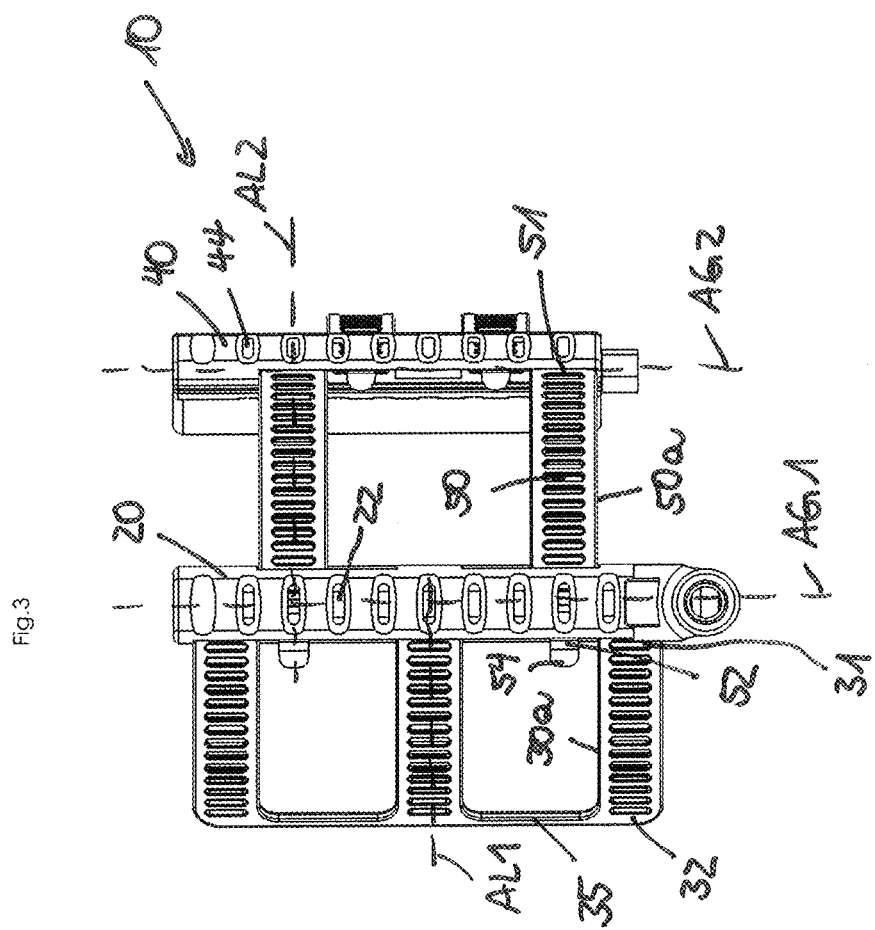

FIGS. 1 to 7 show different views of an embodiment example of a surgical retractor 10 according to the present disclosure for cardiac surgery. Identical reference numbers denote identical or functionally identical parts, wherein for a clearer overview not all reference numbers are provided in all Figures.

The surgical retractor 10 for cardiac surgery comprises a hollow tube-shaped first base body 20 with a first base body longitudinal axis AG1. The first base body 20 can be composed of two half shells 20a, 20b which can simplify the production and the assembly. On the first base body 20 at least one first rib 30, in the present embodiment example three first ribs 30, comprising a first end 31, a second end 32, and a first base body longitudinal axis AL1, is disposed laterally with its first end 31. The lateral disposition leads in particular to the first rib longitudinal axis AU being disposed substantially transversely, for example substantially perpendicularly, to the first base body longitudinal axis AG1. The second ends 32 of the first ribs 30 can be connected by means of a transverse web 35 in order to improve the stability of retractor 10.

The retractor 10 furthermore comprises a second base body 40 with a second base body longitudinal axis AG2, on which at least one second rib 50, in the present embodiment example two second ribs 50, each comprising a first end 51, a second end 52 and a second rib longitudinal axis AL2, is disposed laterally with its first end 51. The lateral disposition leads in particular to the second rib longitudinal axis AL2 being disposed substantially transversely, for example substantially perpendicularly, to the second base body longitudinal axis AG2.

The second base body 40 can be of a length 132 that is less than a length 131 of the first base body 20, preferably by less than 10% of length 131 of the first base body 20 (cf. FIG. 7).

In the first base body 20 is disposed a first transport rod 25, comprising a first transport rod longitudinal axis AT1, such that it is supported rotatably about the first transport rod longitudinal axis AT1. The first base body 20 can be composed of two half shells 20a, 20b, which can simplify the production and the assembly, in particular the emplacement of the first transport rod 25 into the first base body 20.

The first base body 20 comprises a through hole 24 which in particular extends substantially transversely to the first base body longitudinal axis AG1. The at least one second rib 50 is disposed in the through hole 24. The at least one second rib 50 penetrates in particular the first base body 20 in the through hole 24 transversely to the first base body longitudinal axis AG1 (cf in particular FIG. 5). If, as is the case in the present embodiment example, two second ribs 50 are provided, the first base body 20 preferably comprises two through holes 24, and in each of the through holes 24 is disposed a second rib 50.

The at least one second rib 50 comprises several recesses 53 disposed spaced apart with respect to one another along the second rib longitudinal axis AL2, while the first transport rod 25 comprises at least one projection 26 cooperating with the recesses 53. The recesses 53 are in particular not simply developed as indentations but rather as through recesses 53. The first transport rod 25 preferably comprises several projections 26 which are developed for example in the manner of a toothed wheel (cf. FIGS. 5 and 6). If two second ribs 50 are provided, the first transport rod 25 comprises for each of the second ribs 50 at least one projection 26, preferably several projections 26 each in the manner of a toothed wheel (cf. FIG. 6).

The first transport rod 25 can comprise an out-of-round actuation section 27 which, in the present embodiment example, is developed as actuation section 27 with a hexagonal cross section. The actuation section 27 can project from the base body 20 at a front side 21 of the first base body 20 and therewith is easily accessible (cf. in particular FIGS. 1 and 2).

If the first transport rod 25 is rotated about its first transport rod longitudinal axis AT1 for example by applying a wrench-type tool to the actuation section 27 and executing an appropriate lever movement, then, depending on the rotational direction, by the engagement of the projections 26 into the recesses 53, the second rib 50 is pulled further into the through hole 24 or pushed out of it. The second rib 50 can be pulled in until the second base body 40 is in contact on the first base body 20. To prevent the second rib 50 from being unintentionally rotated out or pushed out of the through hole 24 of the first body 20, an abutment element 54 can be disposed on the second end 52 of the second rib 50. If the abutment element 54 is developed to be elastic as, for example, in the present embodiment example as an elastically springy lip, this can enable an intentional rotating-out by deliberately applying greater force.

During a transport movement, i.e. while the second rib [sic: 50] is pulled in or pushed out, a side edge 50*a* of the at least one second rib 50 can be slidingly guided along a side edge 30*a* of the at least one first rib 30, for example in the manner of a tongue-and-groove joint.

The at least one first rib 30 can also comprise several recesses 33 disposed spaced apart with respect to one another along the first rib longitudinal axis AL1. The recesses 33 are, in particular, not developed as simple indentations but rather as through recesses 53.

The retractor 10, furthermore, can [comprise] a third base body 60 with a third base body longitudinal axis AG3 on which is laterally disposed with its first end 71 at least one third rib 70, in the present embodiment example two third ribs 70, each comprising a first end 71, a second end 72, and a third rib longitudinal axis AL3. The lateral disposition leads in particular to the third rib longitudinal axis AL3 being disposed substantially transversely, for example substantially perpendicularly, to the third base body longitudinal axis AG3.

The third base body 60 can be of a length IG3 which corresponds approximately to the length IG2 of the second base body 40 (cf. FIG. 7).

In the second base body 40 can be disposed a second transport rod 45 comprising a second transport rod longitudinal axis AT2 such that it is supported rotatably about the second transport rod longitudinal axis AT2.

Like the first base body 20, the second base body 40 can also be composed of two half-shells.

The second base body 40 can comprise a through hole 44 which extends in particular substantially transversely to the second base body longitudinal axis AG2. The at least one third rib 70 is disposed in the through hole 44. In particular, the at least one third rib 50 penetrates the second base body 40 in the through hole 44 transversely to the second base body longitudinal axis AG2. If, as in the present embodiment example, two third ribs 70 are provided, the second base body 40 preferably comprises two through holes 44, and in each of the through holes 44 is disposed a third rib 70.

The at least one third rib 70 comprises several recesses 73 disposed spaced apart with respect to one another along the third rib longitudinal axis AL3, while the second transport rod 45 comprises at least one projection 46 cooperating with the recesses 73. The second transport rod 45 in particular comprises several projections 46 which are developed, for example, in the manner of a toothed wheel (cf. FIG. 6). If two third ribs 70 are provided, the second transport rod 45 comprises at least one projection 46, preferably several projections 46, each in the manner of a toothed wheel, for each of the third ribs 70 (cf. FIG. 6).

The second transport rod 45 can have an out-of-round actuation section 47, which, in the present embodiment example, is developed as an actuation section 47 with a hexagonal cross section. The actuation section 47 can project from the base body 40 at a front side 41 of the second base body 40 and therewith is simple of access (cf in particular FIGS. 1 and 2).

When the second transport rod 45 is rotated about its second transport rod longitudinal axis AT2, as is described in conjunction with the first transport rod 25, the third rib 70 is further drawn into the through hole 44 or pushed out of it, depending on the direction of rotation through the engagement of the projections 46 into the recesses 73. The third rib 70 can be drawn in until the third base body 60 is in contact on the second base body 40. To prevent an unintentional rotating out or pushing out of the second rib 70 from the through hole 44 of the second base body 40, on the second end 72 of the third rib 70 an abutment element 74 can be disposed (cf. FIG. 2). If the abutment element 74 is developed to be elastic, for example as in the present embodiment example, as an elastically springy lip, this can enable the intentional rotating out by deliberately applying a greater force.

The width of a rib 30, 50, 70 corresponds preferably approximately to the length IG1 of the first base body 20 divided by the number of all ribs 30, 50, 70 of the retractor 10. The width of a rib 30, 50, 70 can thereby be selected as large as feasible, If the second base body 40 is disposed in contact on the first base body 20, and the third base body 60 in contact on the second base body 40, the second ribs 50 and the third ribs 70 project into the interspaces between the first ribs 30. Herein the two second ribs 50 are especially preferably each in contact on the outer of the three first ribs 30, while the two third ribs 70 are in contact on the inner one of the three first ribs 30, and at their outer side edge are each in contact on one of the two second ribs 50.

Ribs 30, 50, 70 can be developed to be curved along their rib longitudinal axis AL1, AL2, AL3 (cf. in particular FIG. 4). In this case, the through hole 24, 44 can have a curved contact area 24*a* for the particular rib 50, 70 (cf in particular FIG. 5).

The hollow tube-shaped base bodies 20, 40 can comprise at least one flush opening 22, 42, preferably several flush openings 22, 42.

On the retractor 10, in particular on the first base body 20, a receiving element 80 can be disposed for receiving a holding and/or manipulation grip 90 (cf in particular FIG. 7). When the holding and/or manipulation grip 90 is set into the receiving element 80, the retractor 10 can therewith set in through an access into the surgical field and be positioned at the desired position and in the orientation.

LIST OF REFERENCE NUMBERS

10 Retractor
20 First base body
20*a* Half shell
20*b* Half shell
21 Front side
22 Flush opening
24 Through hole
24*a* Contact area
25 First transport rod
26 Projection 27 Actuation section
30 First rib
30a Side edge
31 First end
31[sic 32] Second end
33 Recess
35 Transverse web
40 Second base body
41 Front side
42 Flush opening
44 Through hole
45 Second transport rod
46 Projection
47 Actuation section
50 Second rib
50a Side edge
51 First end
52 Second end
53 Recess
54 Abutment element
60 Third base body
70 Third rib
71 First end
72 Second end
73 Recess
74 Abutment element
80 Receiving element
90 Holding and/or manipulation grip
101 Length
102 Length
103 Length
AG1 First base body longitudinal axis
AG2 Second base body longitudinal axis
AG3 Third base body longitudinal axis
AL1 First rib longitudinal axis
AL2 Second rib longitudinal axis
AL3 Third rib longitudinal axis
AT1 First transport rod longitudinal axis
AT2 Second transport rod longitudinal axis

The invention claimed is:

1. A surgical retractor for cardiac surgery, comprising:
a hollow tube-shaped first base body with a first base body longitudinal axis;
a first rib comprising a first end of the first rib, a second end of the first rib, and a first rib longitudinal axis, wherein the first end of the first rib is laterally disposed on the first base body;
a second base body with a second base body longitudinal axis;
a second rib comprising a first end of the second rib, a second end of the second rib, and a second rib longitudinal axis, wherein the first end of the second rib is laterally disposed on the second base body;
a first transport rod with a first transport rod longitudinal axis disposed in the first base body such that the first transport rod is supported rotatably about the first transport rod longitudinal axis;
wherein the second rib penetrates the first base body in a through hole-P transversely to the first base body longitudinal axis, and wherein the second rib comprises several recesses spaced apart with respect to one another along the second rib longitudinal axis, and the first transport rod comprises a projection cooperating with the recesses.

2. The surgical retractor as in claim 1, wherein the first transport rod comprises several projections implemented as a toothed wheel.

3. The surgical retractor as in claim 1,
wherein the first transport rod comprises an out-of-round actuation section, wherein the actuation section projects from the first base body at a front side of the first base body.

4. The surgical retractor as in claim 1,
wherein the first base body comprises three first ribs disposed spaced apart along the first base body longitudinal axis.

5. The surgical retractor as in claim 1,
wherein the second base body comprises two second ribs disposed spaced apart along the second base body longitudinal axis.

6. The surgical retractor as claim 1,
wherein during a transport movement a side edge of the second rib is guided slidingly along a side edge of the first rib.

7. The surgical retractor as in claim 1,
wherein the second base body is of a length that is at least 10% less than a length of the first base body.

8. The surgical retractor as in claim 1,
further comprising a third base body with a third base body longitudinal axis;
a third rib comprising a first end of the third rib, a second end of the third rib, and a third rib longitudinal axis, wherein the first end of the third rib is laterally disposed on the third base body;
a second transport rod with a second transport rod longitudinal axis disposed in the second base body and supported rotatably about the second transport rod longitudinal axis, wherein the second base body is hollow;
wherein the third rib penetrates the second base body in a through hole transversely to the second base body longitudinal axis, and
wherein the third rib comprises several recesses disposed spaced apart from one another along the third rib longitudinal axis, and the second transport rod comprises at least one projection cooperating with the recesses.

9. The surgical retractor as in claim 8, wherein the third base body comprises two third ribs disposed spaced apart along the third base body axis.

10. The surgical retractor as in claim 8,
wherein the width of the first rib, the second rib, the third, or a combination thereof, corresponds approximately to the length of the first base body divided by the number of all ribs of the retractor.

11. The surgical retractor as in claim 8,
wherein the ribs are curved along their rib longitudinal axis.

12. The surgical retractor as in claim 8,
wherein the through hole has a curved contact area.

13. The surgical retractor as in claim 1,
wherein the second end of the first rib and the second end of the second rib comprise an elastic abutment element.

14. The surgical retractor as in claim 8,
wherein the hollow tube-shaped first base and the hollow tube-shaped second base body comprise a flush opening.

15. The surgical retractor as in claim 1,
wherein on the first base body a receiving element is disposed for receiving a holding and/or manipulation grip.

16. The surgical retractor as in claim 3, wherein the out-of-round actuation section comprises an actuation section with an hexagonal cross section.

17. The surgical retractor as in claim 6, wherein the side edge of the second rib is guided slidingly along a side edge of the first rib in the manner of a tongue-and-groove joint.

* * * * *